(12) United States Patent
Markoll

(10) Patent No.: US 6,524,233 B2
(45) Date of Patent: Feb. 25, 2003

(54) ELECTROMAGNETIC STIMULATION OF CARTILAGE TISSUE

(76) Inventor: Richard Markoll, Denningerstrasse 104, D-81925 Munich (DE)

(*) Notice: Subject to any disclaimer, the term of this patent is extended or adjusted under 35 U.S.C. 154(b) by 0 days.

(21) Appl. No.: 09/827,348

(22) Filed: Apr. 6, 2001

(65) Prior Publication Data
US 2002/0042633 A1 Apr. 11, 2002

Related U.S. Application Data

(63) Continuation of application No. PCT/IB99/01807, filed on Oct. 8, 1999.

(30) Foreign Application Priority Data
Oct. 9, 1998 (DE) .......................... 198 46 685

(51) Int. Cl.[7] .......................... A61N 1/00; A61K 38/21
(52) U.S. Cl. .......................... 600/14; 424/85.6
(58) Field of Search .......................... 600/13, 14, 407; 424/85.1, 85.6

(56) References Cited

U.S. PATENT DOCUMENTS

| | | | | |
|---|---|---|---|---|
| 4,105,017 A | * | 8/1978 | Ryaby et al. | 600/14 |
| 4,315,503 A | * | 2/1982 | Ryaby et al. | 600/14 |
| 4,932,951 A | * | 6/1990 | Liboff et al. | 600/13 |
| 4,993,413 A | * | 2/1991 | McLeod et al. | 600/13 |
| 5,067,940 A | | 11/1991 | Liboff et al. | |
| 5,330,410 A | | 7/1994 | Baylink | |
| 5,620,463 A | | 4/1997 | Drolet | |
| 5,656,598 A | * | 8/1997 | Dunstan et al. | 424/85.1 |
| 5,865,744 A | * | 2/1999 | Lemelson | 600/407 |

FOREIGN PATENT DOCUMENTS

WO  85/00293  1/1985

* cited by examiner

Primary Examiner—Eric F. Winakur
Assistant Examiner—Nikita R Veniaminov
(74) Attorney, Agent, or Firm—Nath & Associates PLLC; Gary M. Nath; Jerald L. Meyer

(57) ABSTRACT

The Invention relates to the use of pulsating electromagnetic signals for stimulating chondrogenesis. The invention especially relates to the use of FGF (Fibroblast Growth Factor) in combination with pulsating electromagnetic signals for stimulating cartilage and chondrogenesis.

6 Claims, 3 Drawing Sheets

ELECTROMAGNETIC STIMULATION OF CARTILAGE TISSUE

Figure 1A:
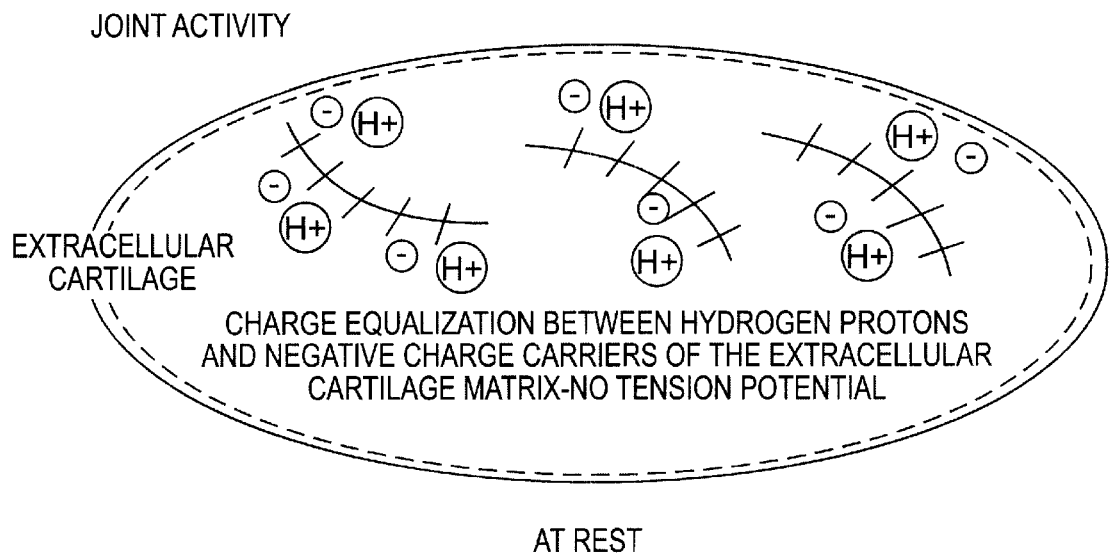
Figure 1B:
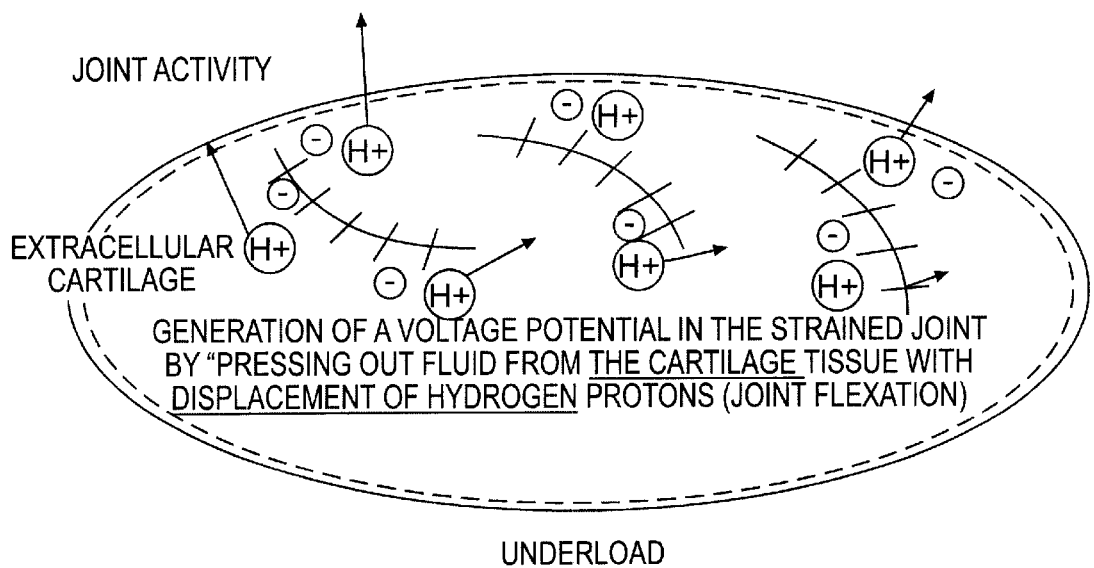
Figure 1C:
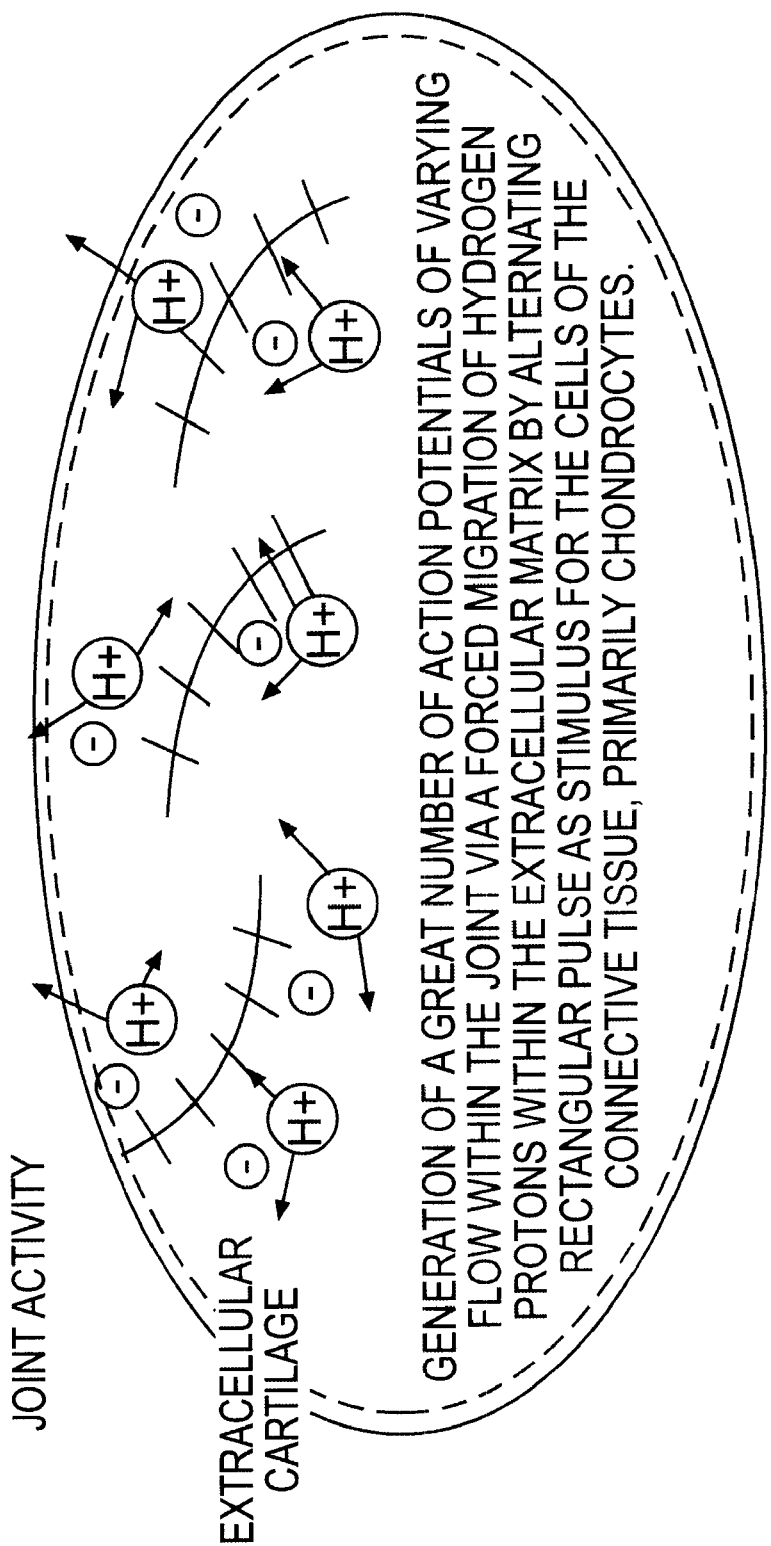
Figure 2A:
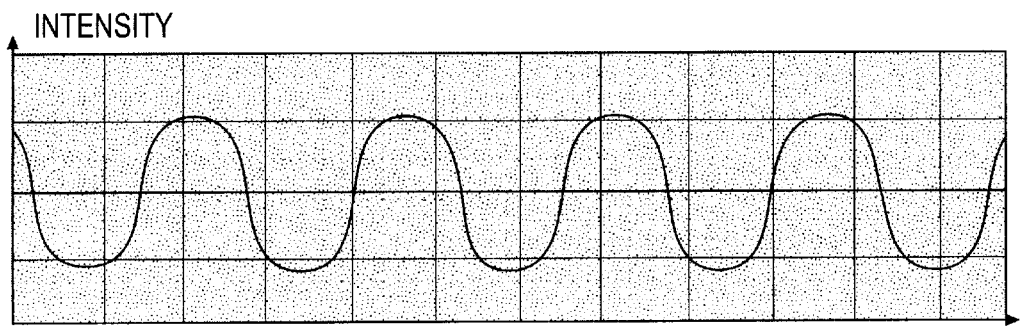
Figure 2B:
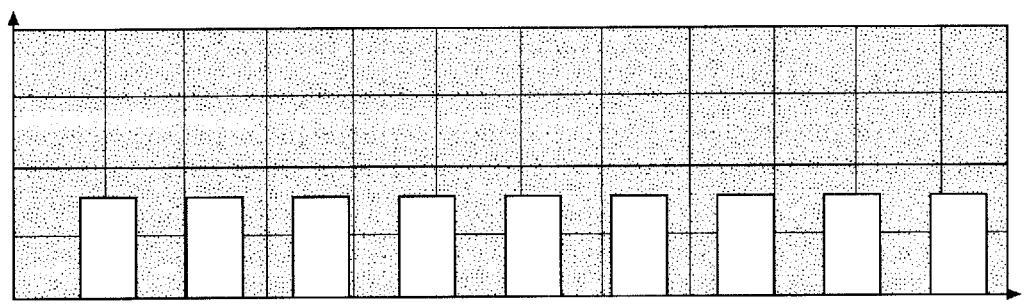
Figure 2C:
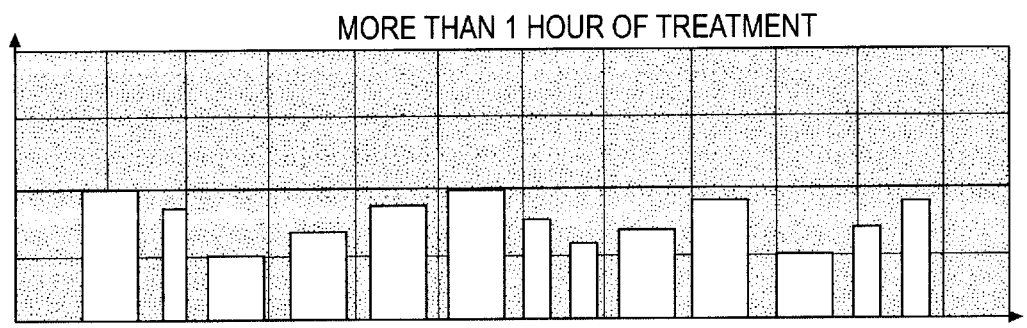

This application is a Continuation of International Application PCT/IB99/01807, with a international filing date of Oct. 8, 1999, the entire contents of the application which is hereby incorporated in its entirety.

SUMMARY OF THE INVENTION

The invention relates to the use of pulsating electromagnetic signals for stimulating chondrogenesis. In particular, it relates to the use of FGF (fibroblast growth factor) in combination with pulsating electromagnetic signals for stimulating cartilage and chondrogenesis.

BACKGROUND OF THE INVENTION

It is known that under physiological conditions healthy cartilage of the joints is subject to strain and that this may lead to attrition of cartilage along with destruction of the cartilage surface. Also inactivity and changes in the synovia caused by infection may result in destruction of cartilage.

Cartilage is a structural tissue consisting of chondrocytes, rich in water, and an intercellular substance. 60 to 80% of the extracellular matrix of cartilage consists of water. The intercellular substance is composed of basic substances (proteoglycans and glucoproteins) as well as filaments (collagen). Proteoglycans, glucoproteins and collagen are manufactured by chondrocytes. Collagen forms a texture in which proteoglycans and glucoproteins are embedded and held in place.

There are a number of different kinds of collagen. Collagen molecules of types I, II, III, V, and VI have similar molecular structures. Collagen molecules of types IX, XII, and XIV contain a number of triple helix domains that are interrupted by non-collagen domains. Also there are differences among the various kinds of collagen molecules. Type V collagen molecules have a low alanin content, but a high content in basic amino acids. In addition, they form tetramers. Type VIII is a strong protease. Type IX is found on the surface of collagen type II. Type XI collagen molecules are short triple helices with very long globular extensions. Type VII Collagen molecules have an N-terminal domain region with three fingers similar to collagen types XII and XIV.

Proteoglycans form hydrated gels through which nutrients reach the chondrocytes by diffusion. Proteoglycans are macromolecules, which consist of a protein nucleus to which a number of glycosamine glycan chains are bound. Components of glycose amine glycans comprise disaccharides with negatively charged sulfate and carboxyl groups, which determine the charge density of the extracellular cartilage matrix.

These negative charges are neutralised by sodium ions of the extracellular fluids. For this reason, a considerable amount of sodium is contained in cartilage, giving rise to high osmotic pressure, attracting water, wherefore 80% of cartilage consists of water.

Under pressure, cartilage is compressed, the water is displaced taking with it the mobile sodium ions, while the negatively charged carboxyl and sulfate ions of the proteoglycan are left behind. This process creates an electrical current, since non-neutralized negative charges are present in the cartilage. According to the Donnan effect, the negative charges determine the concentration of gegenions. The negative charges and the electrical current generate an electrical charge. When the pressure is released, sodium ions and water are once more attracted and the cartilage expands once more to its original volume.

Via this mechanism, chondrocytes are stimulated to synthesize additional matrix. Biosynthetic productivity of the chondrocytes depends on extracellular osmolarity, wherefore it may be assumed that mechanical and physio-chemical conditions are important prerequisites for transmission of signals in conjunction with the pressure applied.

Cartilage flow potentials may be altered by reduction of proteoglycan content, for example, by enzymatic decomposition of chondrocytes. Changes in the extracellular matrix therefore must also lead to changes in electrical phenomena so that the chondrocyte receives altered signals, which influence synthesis productivity.

In osteoarthritis, wear and tear of the cartilage occurs so that the matrix is lost. The cartilage can no longer perform its normal functions due to loss of matrix components, since the amount of proteoglycans present is less. In addition, it has been found in the laboratory that afflicted cartilage and other neighboring tissue of the joint swells, and therefore less current can flow.

A so-called magnetic field therapy is known which is applied to non-healing bone fractures. In magnetic field therapy, sinus shaped, continuous alternating current is applied having a frequency of approximately 44 to 77 Hz and field strength of 2 G.

FGF is known to be a growth stimulant for fibroblasts. FGF is subdivided into basic FGF (bFGF) and acidic FGF (aFGF). Basic FGF is present in cartilage and bones and is involved in the development and growth of cartilage. Various forms of bFGF have been reported found in the nucleus and cytoplasm as well as in the extracellular matrix of cells. Application of bFGF induces chondrocyte to multiply and synthesize extracellular matrix (see Cuevas, P., Burgos, J., and Baird, A., Basic Fibroblast Growth Factor (FGF) Promotes In Vivo Cartilage Repair, Biochem. Biophys. Res. Commun., 31, 611, 1988). Also, it was found that injection of aFGF (1 µg/d) at the site of bone fracture increases chondrogenesis and osteogenesis (see Jingushi, S., Heydemann, A., Kana, S. K., Macey, L. R., and Bolander, M. E., Acidic fibroblast growth factor (aFGF) injection stimulates cartilage enlargement and inhibits cartilage gene expression in rat fracture healing, J. Orthop. Res., 8, 364, 1990).

DESCRIPTION OF THE ILLUSTRATIONS

FIG. 1:

Diagram 1: Charge equalization between hydrogen protons and carriers of negative charges in the extracellular cartilage matrix.

Diagram 2: Generation of a voltage potential in the strained joint by "pressing out" fluid from the cartilage tissue with displacement of hydrogen protons.

Diagram 3: Generation of a great number of action potentials of varying flow within the joint via a forced migration of hydrogen protons within the extracellular matrix by alternating rectangular pulse as stimulus for the cells of the connective tissue, primarily chondrocytes.

FIG. 2:

Diagram 1: Diagram of a Krause-Lechner spool working with alternating current magnetic fields generating a sine curve. This is a non-physiological form of energy transfer.

Diagram 2: Diagram showing the application of pulsating electromagnetic fields. A direct current signal is applied that is continuously repeated. It is transmitted at a particular intensity and at a particular frequency. This pulse remains constant for the duration of the development of the joint.

Diagram 3: Diagram with alternating rectangular pulses as stimulus, which are transmitted in alternating directions for the duration of the treatment. The intensity of the rectangular pulses ranges mostly from 0.5 to 1.5 millitessla. The frequency lies within the range of 10 to 30 Hertz. This kind of stimulation is of relatively low frequency as well as low energy with respect to field strength.

DETAILED DESCRIPTION OF THE INVENTION

The object of the invention is regeneration of damaged cartilage. In particular, such regeneration is intended to stimulate production of collagen types that are present in healthy cartilage tissue.

An additional object is the application of FGF to stimulate cartilage tissue of patients concurrently subjected to electromagnetic signals.

According to the invention, the above objects are solved by the subject matter of the claims.

It was found that by using electromagnetic signals generated by pulsing, pulse-modulated, quasi-rectangular direct current, cartilage tissue is particularly well stimulated. The frequency should range from 1 to 30 Hz, preferably 10 to 12 Hz, and the field strength from 10 to 20 G, preferably 12 to 14 G, 12.5 G being particularly preferred. It is particularly advantageous for the modulation to be quasi-rectangular. The electromagnetic signals used according to the invention are pulsating signals. As a result, weak electromagnetic fields are transmitted to the body. They create an electric field. Via these electromagnetic signals thus generated, the damaged cartilage is subjected to an electromagnetic field corresponding to that which is present in healthy cartilage. If this occurs for a certain period of time, cartilage tissue is stimulated in this manner post-injury as is the growth of chondrocytes.

This form of stimulation has the effect that a chondrocyte that due to pathological changes in the extracellular matrix no longer receives physiological signals once again receives signals, and thus the metabolism of connective tissues, hyaline cartilage, fibrous cartilage, ligaments, tendons, joint capsule may be normalized. This is confirmed by clinical observation of significant pain reduction in the application of this therapy.

In the resting state without strain, the use of the signals according to this invention generates a great number of differently flowing potentials in the joint. This is achieved by a changing pattern of rectangular pulses, forcing hydrogen protons into various migrations within the joint region. As a result, a great number of multidirectional potentials are generated leading to an increase in chondrocyte activity.

According to the invention, it is necessary to set the signals of the electromagnetic field such that they approximate natural conditions in cartilage tissue.

Proven indications for the application of such signals are diseases of the motion apparatus such as for example arthritis, tendinitis, family of rheumatic illnesses, rheumatism and acute injuries.

Experimental studies on cartilage explant cultures subjected to electromagnetic signals of an impulse duration of 30 ms, a frequency of 1.5 Hz, and an impulse increase within 230 ms have shown that a well balanced proteoglycan composition remains without any effect on the molecular structure or functions.

Particularly preferred, according to the invention, is the use of FGF to stimulate cartilage tissue of patients that are concurrently exposed to electromagnetic signals generated by pulsating, pulse modulated direct current having a frequency of 1 to 30 Hz and a field strength of 10 to 20 G.

According to the invention, FGF is dispensed intramuscularly, intravenously, or subcutaneously in the application of the pulsating signals to stimulate cartilage tissue.

Moreover, patients receive a dose of up to 100 $\mu$g FGF. Preferably, treatments are carried out in nine one-hour periods on consecutive days if possible.

Furthermore, it was found that in using FGF in patients that were simultaneously exposed to electromagnetic signals having the above-mentioned features, chondrogenesis was stimulated, in particular, synthesis of collagen II, IX, XI, and XII is stimulated.

The energy characteristics applicable to the treatment of cartilage that were proven to be particularly effective are shown in Table I.

TABLE I

| Parameters | PST |
| --- | --- |
| energy form | direct current |
| frequency | 1 to 30 Hz |
| wave form | quasi rectangular |
| field strength | 10 to 20 G |
| pulse frequency | pulse modulated |
| frequency source | six frequency sources |
| implementation | free wheeling diode |
| energy driver | pulsating direct current |
| work cycle | >60 % |

In addition, a number of enzymes and synthesis products were shown to be present in the cartilage or synovial fluid. Based on the concentrations of certain cartilage markers, it may be inferred that degradative and reparative processes take place within the joint cartilage.

Cartilage markers were measured prior to and after treatment with pulsating electromagnetic signals of the type mentioned thus far. The following parameters were determined in the synovial fluid: matrix proteases (collagenases) MMP-I, MMP-III, MMP-VIII, MMP-inhibitor TIMP 1, matrix proteins associated with connective tissue proliferation, tenascin and PII INP, cytokines associated with synovial infection TNF-$\alpha$, TGF-$\beta$1, IL-1, and IL-6, as well as CRP, urea, and the total protein including the albumin fraction.

Also, a marker such as urea or albumin may be measured within the synovial fluid.

Measurement of tenascin provides results on the synthesis and proliferation of cartilage, while MMP-2 provides information with respect to collagen degradation, and TIMP-1 with respect to matrix synthesis.

Changes in the amounts of synthesis and degradation are proven within the joint cartilage. By testing the joint fluid prior to and after treatments, a positive effect of the electromagnetic signals according to the invention on cartilage metabolism could be shown.

What is claimed is:

1. A method for stimulating regeneration of cartilage tissue and chondrogenesis by stimulating synthesis of collagen II, IX, XI and XII comprising the steps of:

administering fibroblast growth factor (FGF) to a patient; and simultaneously exposing the patient to electromagnetic signals generated by pulsating, impulse-modulated quasi rectangular direct current to a damaged cartilage at a frequency of 1 to 30 Hz and a field strength 10 to 20 G.

2. Method according to claim 1 characterized in that the frequency is equal to 10 to 12 Hz.

3. Method according to claim 1 characterized in that the field strength is equal to 12 to 14 G.

4. Method according to claim 3 characterized in that the field strength is equal to 12.5 G.

5. Method according to claim 1 where the electromagnetic signals, being a product of amplitude with a time varying interval that rises abruptly, maintains a relatively flat top for an interval and rapidly falls to zero, are modulated.

6. Method according to claim 1 wherein said FGF is dispensed intramuscularly, intravenously, or subcutaneously.

* * * * *